United States Patent [19]

Hochlowski et al.

[11] Patent Number: 5,767,096
[45] Date of Patent: Jun. 16, 1998

[54] BROMOTIACUMICIN COMPOUNDS

[75] Inventors: Jill E. Hochlowski, Green Oaks; Marianna Jackson, Waukegan; James B. McAlpine, Libertyville, all of Ill.; Ronald R. Rasmussen, Burlington, Wis.

[73] Assignee: Abbott Laboratories, Abbott Park, Ill.

[21] Appl. No.: 678,906

[22] Filed: Jul. 12, 1996

[51] Int. Cl.$^6$ ............................................. A61K 31/71
[52] U.S. Cl. ........................ 514/28; 536/7.1; 536/16.8; 435/75; 435/76
[58] Field of Search .................. 536/1.1, 7.1, 16.8; 574/28; 435/75, 76

[56] References Cited

U.S. PATENT DOCUMENTS 4,918,174  4/1990  McAlpine et al. ..................... 536/7.1

OTHER PUBLICATIONS

Journal of Antibiotics, vol. 41, No. 3 (Mar. 1988), pp. 308–315, Cavalleri et al., "Structure and Biological Activity of Lipamycin B.".

Journal of Antibiotics, vol. 39, No. 10 (1986), pp. 1407–1412, Omura et al., "Clostomicins, New Antibiotics Produced by mecromonospora Echinospora Subsp. Armeniaca Subsp. No.".

*Primary Examiner*—Elli Peselev
*Attorney, Agent, or Firm*—Mona Anand

[57] ABSTRACT

Antimicrobial compounds having the formula

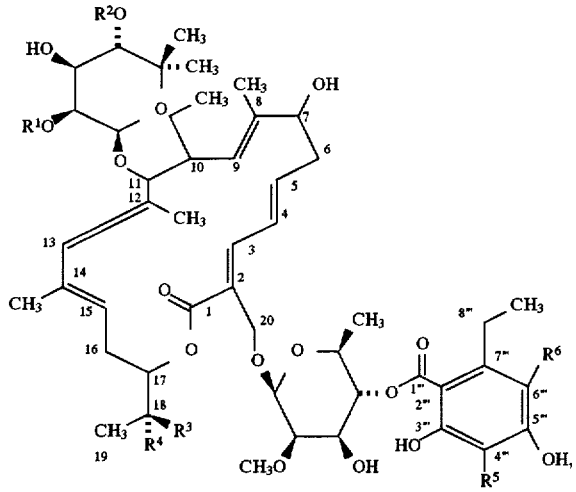

wherein
$R^1$ and $R^2$ are independently selected from the group consisting of hydrogen and $C_1$-to-$C_4$ alkanoyl;
$R^3$ and $R^4$ are selected from the group consisting of
  (a) $R^3$ is hydrogen and $R^4$ is hydroxy,
  (b) $R^3$ is hydroxy and $R^4$ is hydrogen,
  (c) $R^3$ and $R^4$ taken together are =O; or selected from the group consisting of hydrogen and hydroxy; and
$R^5$ and $R^6$ are independently selected from the group consisting of hydrogen, bromine and chlorine, with the proviso that at least one of $R^5$ and $R^6$ must be bromine. Also disclosed are pharmaceutical compositions comprising such compounds, methods of treating bacterial infection by the administration thereof and a process for preparing said compounds.

14 Claims, No Drawings

BROMOTIACUMICIN COMPOUNDS

TECHNICAL FIELD

The present invention relates to new bromotiacumicin antibiotics, pharmaceutical compositions containing such compounds, the use thereof in treating bacterial infections and a process for their preparation.

BACKGROUND OF THE INVENTION

Certain antibiotics which are active against a broad range of Gram-positive and other bacteria are known to be produced by species of micro-organisms isolated from soil samples throughout the world. There is an ongoing need, however, for new antimicrobial agents which show improved activity, have an improved or specific spectrum of efficacy, and/or exhibit more desirable pharmacokinetic properties when administered to a patient.

There is a particular need for antimicrobial agents which are useful in treatment of antibacterial-associated or other nosocomial colitis, often caused by the organism *Clostridium difficile*, especially while still permitting the re-establishment of some or all of the normal flora.

Tiacumicin antibiotics are described in U.S. Pat. No. 4,918,174 (issued Apr. 17, 1990 and incorporated herein by reference), and comprise the compounds tiacumicin A, tiacumicin B, tiacumicin C, tiacumicin D, tiacumicin E and tiacumicin F. Related compounds are the lipiarmycin antibiotics (cf., Arnone et al., *J. Chem Soc. Perkin Trails. I*, 1987:1353–1359 (1987) and Cavalleri et al., *J. Antibiotics*, 41:308–315 (1988)) and the clostomicin antibiotics (cf., Omura et al., *J. Antibiotics*, 39:1407–1412 (1986)).

SUMMARY OF THE INVENTION

It has now been established that novel bromotiacumicin antimicrobial agents may be obtained by modification of the process for producing tiacumicin antibiotics, which are isolated from the fermentation broth and mycelium of *Dactylosporangium aurantiacun* subsp. *hamdenensis* subsp. nov. The compounds of the present invention, which are brominated derivatives of the above tiacumicins, are found to have in vitro activity against a variety of bacterial pathogens and in particular against Clostridium when evaluated in an assay utilizing Wilkins-Chalgren agar in anaerobic conditions. It is therefore expected that these compounds will be useful in the treatment of bacterial infections in mammals.

In one aspect of the invention are compounds having the formula (I)

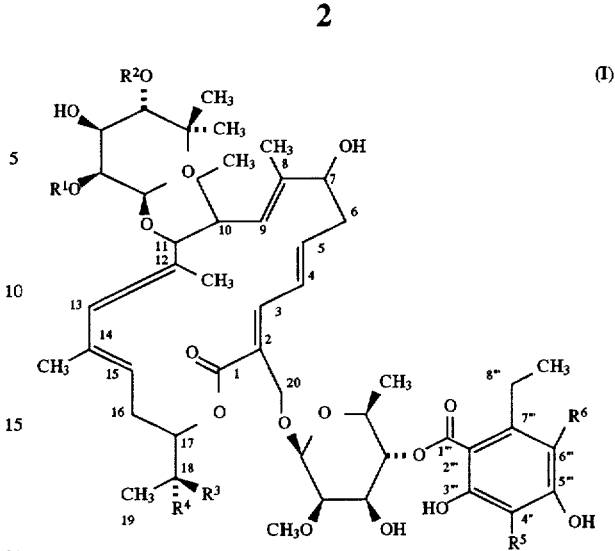

or pharmaceutically acceptable prodrugs thereof, wherein
$R^1$ and $R^2$ are independently selected from the group consisting of hydrogen and $C_1$-to-$C_4$ alkanoyl;
$R^3$ and $R^4$ are selected from the group consisting of
(a) $R^3$ is hydrogen and $R^4$ is hydroxy,
(b) $R^3$ is hydroxy and $R^4$ is hydrogen, and
(c) $R^3$ and $R^4$ taken together are =O;
$R^5$ and $R^6$ are independently selected from the group consisting of hydrogen, bromine and chlorine, with the proviso that at least one of $R^5$ and $R^6$ must be bromine.

In a further aspect of the present invention, pharmaceutical compositions are disclosed which comprise a therapeutically effective amount of a compound of the invention in combination with a pharmaceutically acceptable carrier.

In another aspect of the invention is disclosed a method of treating a Gram-positive bacterial infection, and particularly one caused by the pathogen *Clostridium difficile*, in a patient in need of such treatment, comprising administering to the patient a therapeutically effective amount of a compound of the invention.

In still another aspect of the invention is disclosed a process for preparing the compounds of the invention which comprises the steps of (a) isolating a bromotiacumicin from a bromide enriched fermentation medium and (b) purification of the bromotiacumicin by precipitation or other methods.

DETAILED DESCRIPTION OF THE INVENTION

In one preferred embodiment of the invention are those compounds of formula (I) wherein one of $R^1$ and $R^2$ is $C_1$-to-$C_4$ alkanoyl and the other is hydrogen.

In another preferred embodiment of the invention are those compounds of formula (I) wherein $R^5$ is bromine and $R^6$ is hydrogen.

In yet another preferred embodiment of the invention are those compounds of formula (I) wherein $R^5$ is chlorine and $R^6$ is bromine.

Representative of compounds of the present invention are the following:
Compound of formula (I) wherein $R^1$ is hydrogen and $R^2$ is 2-methylpropanoyl, $R^3$ is hydrogen, $R^4$ is hydroxy, $R^5$ is chlorine and $R^6$ is bromine;
Compound of formula (I) wherein $R^1$ is hydrogen and $R^2$ is 2-methylpropanoyl, $R^3$ and $R^4$ taken together are =O, $R^5$ is chlorine and $R^6$ is bromine;

Compound of formula (I) wherein $R^1$ is hydrogen and $R^2$ is 2-methylpropanoyl, $R^3$ is hydrogen, $R^4$ is hydroxy, $R^5$ is bromine and $R^6$ is hydrogen; and Compound of formula (I) wherein $R^1$ is 2-methylpropanoyl and $R^2$ is hydrogen, $R^3$ is hydrogen, $R^4$ is hydroxy, $R^5$ is bromine and $R^6$ is hydrogen; or a pharmaceutically acceptable prodrug thereof.

The best mode of the invention is the compound of formula (I) wherein $R^1$ is hydrogen and $R^2$ is 2-methylpropanoyl, $R^3$ is hydrogen, $R^4$ is hydroxy, $R^5$ is chlorine and $R^6$ is bromine.

As used throughout this specification and in the appended claims, the following terms have the meanings specified:

The term "alkyl" as used herein refers to a monovalent straight-chain or branched-chain hydrocarbon radical of 1 to 12 carbon atoms including, but not limited to, methyl, ethyl, n-propyl, isopropyl, n-butyl, sec-butyl, isobutyl, tert-butyl, pentyl, hexyl, heptyl and the like.

The term "alkanoyl" as used herein refers to a monovalent radical of the formula —C(O)R", where R" is hydrogen or an alkyl group as defined above, including but not limited to acetyl, propionyl, isobutyryl and the like.

The term "$C_1$-to-$C_4$ alkanoyl" as used herein refers to an alkanoyl radical as defined above where R" is hydrogen or an alkyl group of 1 to 3 carbon atoms.

The term "lower alkyl" as used herein refers to an alkyl radical as defined above having 1 to 6 carbon atoms.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexyl-carbodiimide) method, the active ester method (p-nitrophenyl ester method, N-hydroxy-succinic acid imide ester method, cyanomethyl ester method and the like), the Woodward reagent K method, the DCC-HOBT (1-hydroxy-benzotriazole) method and the like. Classical methods for amino acid condensation reactions are described in M. Bodansky, Y. S. Klausner and M. A. Ondetti, *Peptide Synthesis*, Second Edition, NY, 1976.

Asymmetric centers may exist in the compounds of the present invention. Except where otherwise noted, the present invention contemplates the various stereoisomers and mixtures thereof. Accordingly, whenever a bond is represented nonstereospecifically, it is intended to encompass both orientations.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat the targeted disorder, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal by oral administration may range from about 0.01 to about 100 mg/kg/day. More preferable doses may be in the range of from about 0.1 to about 10 mg/kg/day. If desired, the effective daily dose may be divided into multiple doses for purposes of administration; consequently, single dose compositions may contain such amounts or submultiples thereof as make up the daily dose.

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, or drops), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection include pharmaceutically acceptable sterile nonaqueous solutions or aqueous dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose and acacia, c) humectants such as glycerol, d) disintegrating agents such as agar-agar, calcium carbonate, potato or tapioca starch, alginic acid, certain silicates and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols and sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, and sweetening, flavoring and perfuming agents.

Suspensions, in addition to the active compounds, may contain suspending agents as, for example, ethoxylated isostearyl alcohol, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y., 1976, p. 33 et seq.

Processes for Preparing BROMOTIACUMICIN

The compounds of the invention may be prepared using one or more of the processes which follow. The fermentation process for tiacumicins is described in the above-referenced U.S. Pat. No. 4,918,174. The preparation of the BROMOTIACUMICIN may be achieved by modification of the above-mentioned process by the replacement of sodium chloride with sodium bromide in the fermentation medium. The sodium bromide concentration of the medium may be in the range of 0.25–1.0%, and most preferably about 0.48%.

The bromotiacumicins can be extracted from the fermentation beer with common organic solvents immiscible or only partially miscible with water such as ethyl acetate, diethyl ether, methylene chloride or chloroform. It is preferable to lyse the mycelia by addition of moderate amounts of water miscible solvent such a methanol or acetone prior to performing the extraction. This step ensures extraction of antibiotic from intramycelial reservoirs. Separation of congenic tiacumicin antibiotics can be effected by chromatographic methods.

Experimental

Optical rotations were measured on a Perkin-Elmer Model 241 polarimeter in a 10 cm cell. Fast atom bombardment mass spectra were measured on a Kratos MS-50 mass spectrometer. Ultraviolet spectra were recorded on a Perkin-Elmer Lambda 3B UV-visible spectrophotometer and infrared spectra on a Nicolet model 60SX FT-IR attached to a Nicolet computer. NMR spectra were acquired on either a General Electric GN500 or GN300 spectrometer. NMR spectral data are reported in Table 1 (following Example 6 below). $R_f$ values reported were acquired on Analtech TLC plates developed with chloroform:methanol (9:1, v:v) and were visualized using ceric sulfate spray reagent. Melting points were determined on a Hoover Unimelt and are reported uncorrected. Minimal inhibitory concentrations were determined by twofold agar dilution. Brain heart infusion agar was used for aerobes and Wilkins-Chalgren agar for anaerobes.

The compounds, processes and uses of the present invention will be better understood in connection with the following examples, which are intended as an illustration of and not a limitation upon the scope of the invention.

EXAMPLE I

Fermentative Production of Bromotiacumicins

The brominated tiacumicins were produced by submerged fermentation in a 42-liter stainless steel fermentor (LH Fermentation) in a medium consisting of glucose monohydrate 2%, soybean oil 0.1%, soybean flour 1%, beef extract 0.3%, $K_2HPO_4$ 0.05%, $MgSO_4 \cdot 7H_2O$ 0.05%, KBr 0.48% and $CaCO_3$ 0.3%. This formulation is similar to that used for the production of tiacumicins in the above-referenced U.S. Pat. No. 4,918,174 with the substitution of KBr for KCl. The fermentor was charged with 30 liters of medium. Sterilization was at 121° C. and 1.05 kg/cm² for 1 hr. The glucose monohydrate was sterilized separately and added to the fermentor prior to inoculation. The producing organism, *Dactylosporangium aurantiacum* subsp. *hamdenensis* AB 718C-41, was grown on agar slants of ATCC medium 172 for 10 days at 30° C. The slant growth was used to inoculate a seed medium consisting of glucose monohydrate 0.1%, soluble starch 2.4%, yeast extract 0.5%, tryptone 0.5%, beef extract 0.3% and $CaCO_3$ 0.4%. The inoculum was prepared in two steps. The first step, inoculated with slant growth, was incubated for 96 hours. This vegetative growth was used at 5% to inoculate 2-liter Erlenmeyer flasks containing 600 ml of the seed medium. These flasks were incubated for 72 hr. Both steps were incubated at 30° C. on a rotary shaker at 225 rpm (5.08 cm stroke). The second step growth was used at 5% to inoculate the fermentor. During fermentation the temperature was controlled at 30° C., agitation was 250 rpm, the air flow was 0.7 vol/vol/minute and the head pressure was maintained at 0.35 kg/cm². Foam was controlled with a silicone antifoam, XFO 371 (Ivanhoe Industries), added initially at 0.01% and then available on demand. The fermentation was harvested after seven days. At harvest the pH which was 7.9 was adjusted to 7.0.

EXAMPLE 2

Isolation of the Bromotiacumicins

At harvest, whole broth (30 liters) was adjusted to pH 7 and acetone (15 liters) was added. After an hour of agitation, the acetone and fermentation broth mix was extracted with ethyl acetate (3×15 liters). Combined extracts were concentrated to dryness, and the residue was partitioned between chloroform-methanol-water (1200 ml of each). The lower layer of this partition was concentrated to leave a pale amorphous solid. This solid was loaded onto a silica gel column and eluted with a stepwise gradient of from 1% to 50% methanol in chloroform. Active fractions were combined based upon TLC analysis into three pools. The first pool was loaded onto a silica gel column and eluted with successive step gradients of 10%, 20% and 50% methanol in chloroform. Active fractions from this column were combined and concentrated to leave a white solid. This solid was subjected to countercurrent chromatography on an Ito multi-layered coil planet centrifuge in a solvent system of chloroform-carbon tetrachloride-methanol-water (7:3:7:3) with the lower phase stationary. Active fractions from this column were combined and concentrated to yield 2 mg of pure compound 3 (see Example 5 below). Similar chromatography of the second pool gave pure tiacumicin B (58 mg) and pure compound 2 (3 mg) (see Example 4 below). The third pool was subjected to countercurrent chromatography under the same conditions to pure compound 4 (45 mg) (see Example 6 below), and crude compound 1 which was purified by chromatography on a Sephadex LH-20 column and eluted with methylene chloride-methanol (1:1). Active fractions from this LH-20 column were combined and concentrated to yield 42 mg of pure compound 1 (see Example 3 below).

EXAMPLE 3

Characterization of Compound 1; Compound of Formula (I) wherein $R^1$ is hydrogen and $R^2$ is 2-methylpropanoyl, $R^3$ is hydrogen, $R^4$ is hydroxy, $R^5$ is chlorine and $R^6$ is bromine The fast atom bombardment (FAB) positive ion mass spectrum of 1 had a highest molecular weight ion at m/z=1123. As this highest peak could be shifted to m/z=1139 by the addition of potassium to the sample, it is assumed that 1123 is the sodium salt of a parent compound which has a molecular weight of 1100 (Mass-Na). The isotope distribution pattern represented by the 1123 ion cluster could be matched to that of a formula containing one bromine and one chlorine atom. As a molecular weight of 1100 corresponds to a difference in molecular weight from the original tiacumicins of 44 mass units (the difference in atomic weight between bromine and chlorine), this is interpreted as representing the substitution of one bromine in compound 1 for one chlorine atom. A substantial fragmentation peak observed in the positive ion mass spectrum at m/z=437 displays an isotopic distribution pattern corresponding to one bromine and one chlorine atom. This is analogous to the m/z=393 peak with a dichloro isotopic pattern observed in the mass spectrum of the tiacumicins and assigned to the sugar fragment along with its attached aromatic ring (a, b below).

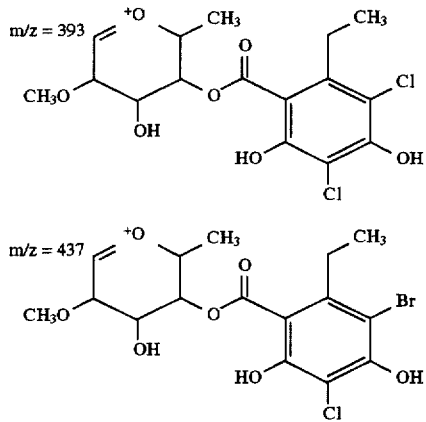

A $^1$H NMR spectrum of compound 1 along with a correlation spectroscopy (COSY) experiment suggested a basic structure essentially equivalent to that for tiacumicin B (See Table 1.) The only difference of note between the PMR spectra of tiacumicin B and compound 1 lies in the C-8''' proton signals of the two. In tiacumicin B, these two proton signals appear as a symmetric complex 2H multiplet centered at d 2.95. In compound 1 the corresponding proton signals appear as 1H pentets at d 3.04 and d 2.97. These data would suggest that compound 1 contains a bromine at C-6''' on the aromatic ring (6'''-dechloro-6'''bromotiacumicin B).

$[a]_D^{25}$ =+3° (c=0.33, MeOH), white amorphous solid, mp 145°–151° C., $R_f$=0.34. MW 1123 (sodium salt). UV (MeOH): $1_{max}$ 224 nm (e 9,900), 232 (shoulder) (9,700), 266 (shoulder) (5,900), 314 (2,400), in acidic methanol $1_{max}$ 206 nm (shoulder) (e 9,400), 222 (11,000), 230 (shoulder) (10,800), 266 (6,500), in basic methanol at $1_{max}$ 206 nm 13,500), 226 (shoulder) (10,300), 232 (10,800), 312 (10,100). IR $u_{max}$ (CDCl$_3$): 3690, 3605, 3665, 3497, 2976, 2935, 2876, 1733, 1684, 1601, 1575, 1468, 1456, 1411, 1385, 1371, 1322, 1312, 1244, 1196, 1159, 1143, 1113, 1087 and 1023 cm$^{-1}$.

EXAMPLE 4

Characterization of Compound 2; Compound of Formula (I) wherein R$^1$ is hydrogen and R$^2$ is C$_1$-to-C$_4$ alkanoyl, R$^3$ and R$^4$ taken together are =O, R$^5$ is chlorine and R$^6$ is bromine The fast atom bombardment (FAB) positive ion mass spectrum of compound 2 had a highest molecular weight ion at m/z=1021. This was shifted to m/z=1037 by the addition of potassium and the molecular weight of compound 2 was therefore assumed to be 1098 or two mass units lower than compound 1. The isotopic distribution pattern of the sodium adduct of compound 2 suggested that this structure contained one bromine and one chlorine atom.

A comparison of the PMR and COSY spectra of compounds 1 and 2 revealed that the two differed in the C-15 to C-19 region. The series of coupled proton signals which define atoms C-15 to C-19 in compound 1 are terminated at C-17 in compound 2, where the d 5.13 proton signal shows coupling only to the methylene protons on C-16. Further, the doublet methyl proton signal for C-19 in compound 1 at d 1.16 is replaced with a singlet methyl proton signal at d 2.21. These data are interpreted as an oxidation at C-18 in compound 2 relative to compound 1. This structure therefore could be described as 6'''-dechloro-6'''-bromo-18-ketotiacumicin B.

$[a]_D^{25}$ =+13° (c=0.21, MeOH), white amorphous solid, mp 139°–144° C., $R_f$=0.35. MW 1121 (sodium salt). UV (MeOH): $1_{max}$ 222 nm (e 10300), 266 (6800), in acidic methanol $1_{max}$ 222 nm (e 8,800), 230 (shoulder) (8,500), 240 (shoulder) (8,200), 316 (shoulder) (5,500) in basic methanol at $1_{max}$ 206 nm (e 13,600), 238 (10,800), 270 (shoulder) (6,700), 316 (4,600). IR $u_{max}$ (CDCl$_3$): 3690, 3608, 2974, 2931, 2874, 1705, 1601, 1457, 1383, 1376, 1312, 1251, 1196, 1162, 1147, 1136, 1111, 1068 and 1022 cm$^{-1}$.

EXAMPLE 5

Characterization of Compound 3; Compound of Formula (I) wherein R$^1$ is hydrogen and R$^2$ is C$_1$-to-C$_4$ alkanoyl, R$^3$ is hydrogen, R$^4$ is hydroxy, R$^5$ is bromine and R$^6$ is hydrogen The molecular weight of compound 3 was established as 1064. The isotopic distribution pattern observed in the sodium adduct of the mass spectrum suggested that compound 3 contained one bromine atom and no chlorine atoms. A substantial fragmentation peak observed in the positive ion mass spectrum at m/z=403 displays an isotopic distribution pattern corresponding to one bromine. This is analogous to the m/z=393 peak with a dichloro isotopic pattern observed for the sugar fragment (c, below) in the mass spectrum of the tiacumicins. A comparison of the proton and COSY spectra of compounds 1 and 3 revealed that these two differed only in the aromatic ring portion of their structures. In particular, compound 3 contained a singlet methine proton signal at d 6.35 which showed one-bond coupling in an HMQC experiment to a carbon signal at d 111.5. This same proton signal (d 6.35) showed three-bond coupling in an HMBC experiment to the 8''' methylene carbon signal at d 27.7 as well as to two aromatic carbon signals at d 98.0 (Q) and d 107.6 (Q). These data indicate that this proton must be on carbon 6''' in compound 3 and established the structure as 4''',6'''-didechloro-4'''-bromotiacumicin B.

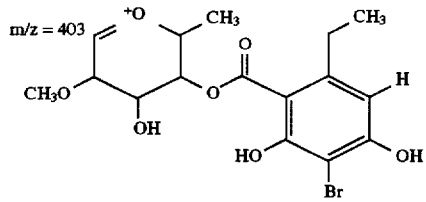

$[a]_D^{25}$ =+3° (c=0.16, MeOH), white amorphous solid, mp 138°–140° C., $R_f$=0.42. MW 1087 (sodium salt). UV (MeOH): $1_{max}$ 226 nm (e 6,000), 266 (3,800), in acidic methanol at $1_{max}$ 226 nm (e 6,700), 266 (4,200) in basic methanol at $1_{max}$ 206 nm (e 7,700), 236 (6,300), 278 (shoulder) (3,800), 304 (3,600), 312 (shoulder) (3,500). IR $u_{max}$ (CDCl$_3$): 3690, 3606, 3501, 2987, 2935, 2875, 1731, 1692, 1653, 1603, 1570, 1469, 1456, 1423, 1386, 1323, 1312, 1295, 1256, 1233, 1187, 1162, 1116, 1069, 1022 and 789 cm$^{-1}$.

EXAMPLE 6

Characterization of Compound 4; Compound of Formula (I) wherein R$^1$ is C$_1$-to-C$_4$ alkanoyl and R$^2$ is hydrogen, R$^3$ is hydrogen, R$^4$ is hydroxy, R$^5$ is bromine and R$^6$ is hydrogen The molecular weight and isotopic distribution pattern of the parent peak of compound 4 was identical to that of compound 3 with a molecular weight of 1064 and one bromine as the only halogen. The same m/z=403 (5c) fragmentation peak with isotopic pattern indicative of a single bromine atom is observed in the mass spectrum of compound 4. A comparison of the proton and COSY spectra of compound 4 to tiacumicin C revealed that these two differed only in the aromatic ring portion of their structures. A comparison of the proton and COSY spectra of compound 4 to compound 3 revealed that these two differed only in the sugar moieties attached at C-11 in these two. Compound 4 contained a singlet methine proton signal at d6.39 which showed one-bond coupling to a carbon signal at d111.8. This same proton signal (d 6.39) showed three-bond coupling to the 8'" methylene carbon signal at d 31.0. These data would support a structure of 4'",6'"-didechloro-4'"-bromotiacumicin C for compound 4.

$|a|_D^{25}$=−5° (c=0.42, MeOH), white amorphous solid, mp 143°–150° C., $R_f$=0.30. MW 1087 (sodium salt). UV (MeOH): $1_{max}$ 226 nm (e 11,500), 266 (7,600), 306 (shoulder) (2,300), in acidic methanol at $1_{max}$ 226 nm (e 11,800), 266 (7,800), 306 (shoulder) (2,000) in basic methanol at $1_{max}$ 204 nm (e 11,500), 226 (shoulder) (10,400), 238 (11,800), 270 (6,500), 306 (7,200). IR $u_{max}$ (CDCl$_3$): 3619, 2976, 2935, 2895, 1733, 1700, 1652, 1646, 1603, 1447, 1388, 1371, 1323, 1311, 125, 1188, 1160, 1145, 1114, 1068 and 1047 cm$^{-1}$.

TABLE 1

$^1$H NMR Assignments for Compounds of Examples 3–6
Chemical shifts are given in parts per million downfield from TMS.
Coupling constants (J values) are in Hz.

| H on C No. | Cmpd of Ex. 3 | Cmpd of Ex. 4 | Cmpd of Ex. 5 | Cmpd of Ex. 6 |
|---|---|---|---|---|
| 3 | 7.21 (d,J=11.2) | 7.42 (d,J=11.6) | 7.21 (d,J=11.2) | 7.18 (d,J=11.7) |
| 4 | 6.59 (dd, J=14.8,11.2) | 6.64 (dd, J=15.2,11.6) | 6.59 (dd, J=14.3,11.2) | 6.58 (dd, J=14.8,11.2) |
| 5 | 5.94 (ddd, J=14.7,9.8,5.4) | 6.08 (ddd, J=15.2,7.6,6.7) | 5.94 (ddd, J=14.3,9.4,4.9) | 5.92 (ddd, J=14.8,9.8,5.3) |
| 6 | 2.70 (mult) 2.49 (mult) | 2.70 (mult) 2.53 (mult) | 2.66 (mult) 2.48 (mult) | 2.65 (mult) 2.47 (mult) |
| 7 | 4.21 (br mult) | 4.26 (br mult) | 4.21 (br mult) | 4.20 (br mult) |
| 9 | 5.13 (br d, J=10.3) | 5.21 (br d, J=10.7) | 5.13 (br d, J=10.7) | 5.10 (dt, J=11.2,1.8) |
| 10 | 2.70 (mult) | 2.70 (mult) | 2.68 (mult) | 2.55 (ddd, J=13.0,8.4,3.1) |
| 11 | 3.69 (d,J=10.3) | 3.73 (d,J=10.2) | 3.70 (d,J=10.3) | 3.65 (d,J=9.8) |
| 13 | 5.82 (br s) | 5.89 (br s) | 5.82 (br s) | 5.83 (br s) |
| 15 | 5.57 (t,J=8.0) | 5.34 (dd, J=9.4,7.2) | 5.57 (br t, J=8.0) | 5.57 (br t, J=8.0) |
| 16 | 2.70 (mult) 2.42 (mult) | 2.80 (mult) 2.70 (mult) | 2.70 (mult) 2.41 (mult) | 2.74 (mult) 2.42 (mult) |
| 17 | 4.71 (mult) | 5.13 (dd, J=9.8,3.6) | 4.68 (mult) | 4.72 (ddd, J=6.4,4.8,4.5) |
| 18 | 4.01 (pentet, J=6.3) | | 4.01 (pentet, J=6.7) | 4.03 (pentet, J=7.0) |
| 19 | 1.16 (d,J=6.7) | 2.21 (s) | 1.17 (d,J=6.7) | 1.20 (d,J=7.0) |
| 20 | 4.60 (d,J=11.6) 4.42 (d,J=11.6) | 4.58 (d,J=11.6) 4.50 (d,J=11.6) | 4.61 (d,J=11.6) 4.42 (d,J=11.6) | 4.61 (d,J=11.6) 4.41 (d,J=11.6) |
| 21 | 1.64 (br s) | 1.62 (br s) | 1.64 (br s) | 1.63 (br s) |
| 22 | 2.00 (mult) 1.25 (mult) | 2.02 (mult) 1.29 (mult) | 1.99 (mult) 1.27 (mult) | 1.82 (mult) 1.14 (mult) |
| 23 | 0.87 (t,J=7.2) | 0.86 (t,J=7.6) | 0.87 (t,J=7.6) | 0.80 (t,J=7.6) |
| 24 | 1.80 (br s) | 1.87 (br s) | 1.80 (br s) | 1.76 (br s) |
| 25 | 1.75 (br s) | 1.68 (br s) | 1.75 (br s) | 1.76 (br s) |
| 1' | 4.62 (s) | 4.62 (br s) | 4.65 (br s) | 4.65 (br s) |
| 2' | 3.54 (mult) | 3.58 (mult) | 3.56 (mult) | 3.56 (mult) |
| 2'-OCH$_3$ | 3.54 (s) | 3.58 (s) | 3.56 (s) | 3.55 (s) |
| 3' | 3.72 (dd,J=9.8,3.4) | 3.80 (dd,J=9.8,3.6) | 3.76 (dd,J=9.8,3.6) | 3.76 (dd,J=9.8,3.2) |

TABLE 1-continued $^1$H NMR Assignments for Compounds of Examples 3–6
Chemical shifts are given in parts per million downfield from TMS.
Coupling constants (J values) are in Hz.

| H on C No. | Cmpd of Ex. 3 | Cmpd of Ex. 4 | Cmpd of Ex. 5 | Cmpd of Ex. 6 |
|---|---|---|---|---|
| 4' | 5.11 (t,J=9.8) | 5.13 (d,J=9.8) | 5.13 (t,J=9.8) | 5.14 (dt, J=9.8,3.1) |
| 5' | 3.52 (dq, J=9.8,6.3) | 3.56 (mult) | 3.58 (mult) | 3.56 (mult) |
| 6' | 1.30 (d,J=6.3) | 1.29 (d,J=6.2) | 1.27 (d,J=6.3) | 1.22 (d,J=6.3) |
| 1" | 4.71 (br s) | 4.72 (br s) | 4.70 (br s) | 4.77 (d,J=1.4) |
| 2" | 3.91 (br d, J=2.7) | 3.92 (br d, J=3.2) | 3.91 (br d, J=3.1) | 5.34 (dd, J=3.6,1.3) |
| 3" | 3.69 (dd, J=10.3,2.7) | 3.73 (mult) | 3.70 (d,J=10.3) | 3.74 (dd, J=10.3,4.2) |
| 4" | 5.01 (d,J=10.3) | 5.02 (d,J=10.3) | 5.00 (d,J=10.3) | 3.45 (d,J=10.3) |
| 6" | 1.15 (s) | 1.16 (s) | 1.17 (s) | 1.26 (s) |
| 7" | 1.12 (s) | 1.10 (s) | 1.13 (s) | 1.08 (s) |
| 6'" | | | 6.35 (s) | 6.39 (s) |
| 8'" | 3.04 (pentet, J=7.2) 2.97 (pentet, J=7.2) | 3.15 (br mult) 3.03 (pentet, J=7.2) | 2.83 (mult,2H) | 2.83 (mult,2H) |
| 9'" | 1.20 (t,J=7.2) | 1.14 (t,J=7.2) | 1.19 (mult) | 1.20 (t,J=7.2) |
| 2"" | 2.58 (hept, J=6.7) | 2.61 (hept, J=6.7) | 2.58 (hept, J=7.2) | 2.68 (hept, J=7.2) |
| 3"" | 1.18 (d,J=6.7) | 1.18 (d,J=6.7) | 1.18 (d,J=7.2) | 1.20 (d,J=7.2) |
| 4"" | 1.17 (d,J=6.7) | 1.17 (d,J=6.7) | 1.16 (d,J=7.2) | 1.19 (d,J=7.2) |

EXAMPLE 7

In Vitro Assay of Antibiotic Activity Against Aerobic and Facultative Bacteria For primary screening of compounds of the invention against selected aerobic microorganisms, minimal inhibitory concentrations (MICs) were determined by the following agar dilution method: Series of two-fold dilutions of the test compounds were added to brain heart infusion agar. The agar plates were inoculated with approximately 10$^4$ organisms per spot of each of the organisms to be tested. These inoculated agar plates were then incubated at 37° C. for approximately 20 hours. The MICs were determined as the minimal concentration of test compound (in mg/mL) that inhibited visible growth.

For primary screening of compounds of the invention against anaerobic bacteria such as Clostridium, minimal inhibitory concentrations (MICs) were determined by the following agar dilution method: Series of two-fold dilutions of the test compounds were added to Wilkins-Chalgren agar. The agar plates were inoculated with approximately 10$^5$ organisms per spot of each of the organisms to be tested. The inoculated agar plates were then incubated at 37° C. for approximately 48 hours. The MICs were determined as the minimal concentration of test compound (in mg/mL) that inhibited visible growth.

The data, shown in Table 2, demonstrate that the brominated tiacumicins retain excellent activity against Clostridium strains, but are less active than tiacumicin B against Staphylococcus and Enterococcus. The compound of Example 3, 6'"-dechloro-6'"-bromotiacumicin B, is the most potent of the compounds of this invention and is quite comparable to tiacumicin B.

TABLE 2

MIC Data (μg/mL) for Selected Organisms

| Organism | Tiacumicin B MIC (mg/ml) | Cmpd of Ex. 3 MIC (mg/ml) | Cmpd of Ex. 4 MIC (mg/ml) | Cmpd of Ex. 5 MIC (mg/ml) | Cmpd of Ex. 6 MIC (mg/ml) |
|---|---|---|---|---|---|
| Staphylococcus aureus ATCC 6538P | 0.78 | 6.2 | 50 | 6.2 | 50 |
| Staphylococcus epidermidis 3519 | 1.56 | 6.2 | 100 | 12.5 | 50 |
| Enterococcus faecium ATCC 8043 | 1.56 | 6.2 | 50 | 12.5 | 25 |
| Streptococcus pyogenes EES61 | 6.2 | 6.2 | 50 | 25 | 50 |
| Escherichia coli JUHL | >200 | >200 | >200 | >200 | >200 |
| Bacteroides fragilis ATCC 25285 | >128 | >128 | >128 | >128 | >128 |
| Bacteriodes thetaiotaomicron ATCC 29741 | >128 | >128 | >128 | >128 | >128 |
| Clostridium perfringes ATCC 13124 | 0.06 | 0.03 | 0.015 | <=0.06 | 0.06 |
| Clostridium difficile ATCC 9689 | 0.06 | 0.06 | 0.25 | 0.12 | 0.5 |
| Clostridium difficile ATCC 17857 | 0.12 | 0.06 | 0.25 | 0.25 | 1 |
| Clostridium difficile 2532 | 0.12 | 0.06 | 1 | 0.5 | 2 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art, and may be made without departing from the spirit and scope thereof.

What is claimed is:

1. A compound having the formula

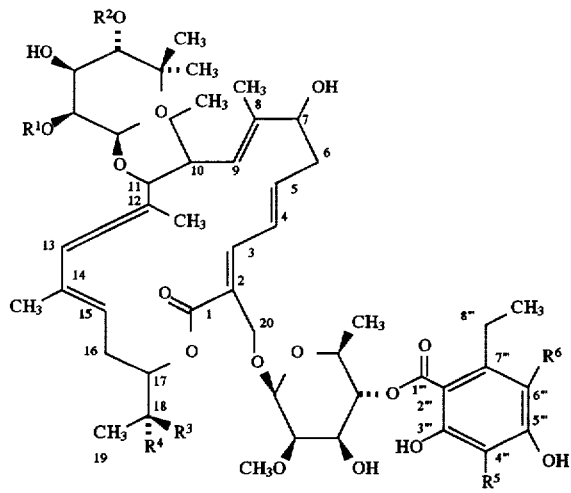

or a pharmaceutically acceptable prodrug thereof, wherein
$R^1$ and $R^2$ are independently selected from the group consisting of hydrogen and $C_1$-to-$C_4$ alkanoyl;

$R^3$ and $R^4$ are selected from the group consisting of
(a) $R^3$ is hydrogen and $R^4$ is hydroxy,
(b) $R^3$ is hydroxy and $R^4$ is hydrogen,
(c) $R^3$ and $R^4$ taken together are =O; or selected from the group consisting of hydrogen and hydroxy; and $R^5$ and $R^6$ are independently selected from the group consisting of hydrogen, bromine and chlorine, with the proviso that at least one of $R^5$ and $R^6$ must be bromine.

2. A compound according to claim 1 wherein one of $R^1$ and $R^2$ is $C_1$-to-$C_4$ alkanoyl and the other is hydrogen.

3. A compound according to claim 1 wherein $R^5$ is bromine and $R^6$ is hydrogen.

4. A compound according to claim 1 wherein $R^5$ is chlorine and $R^6$ is bromine.

5. A compound according to claim 1 which is selected from the group of compounds having the formula according to claim 1 wherein (a) $R^1$ is hydrogen and $R^2$ is 2-methylpropanoyl, $R^3$ is hydrogen, $R^4$ is hydroxy, $R^5$ is chlorine and $R^6$ is bromine;

(b) $R^1$ is hydrogen and $R^2$ is 2-methylpropanoyl, $R^3$ and $R^4$ taken together are =O, $R^5$ is chlorine and $R^6$ is bromine;

(c) $R^1$ is hydrogen and $R^2$ is 2-methylpropanoyl, $R^3$ is hydrogen, $R^4$ is hydroxy, $R^5$ is bromine and $R^6$ is hydrogen; and (d) $R^1$ is 2-methylpropanoyl and $R^2$ is hydrogen, $R^3$ is hydrogen, $R^4$ is hydroxy, $R^5$ is bromine and $R^6$ is hydrogen;

or a pharmaceutically acceptable prodrug thereof.

6. A pharmaceutical composition comprising a therapeutically effective amount of a compound according to claim 1 in combination with a pharmaceutically acceptable carrier.

7. A pharmaceutical composition comprising a therapeutically effective amount of a compound according to claim 5 in combination with a pharmaceutically acceptable carrier.

8. A method of treating a bacterial infection in a patient in need of such treatment, comprising administering to the patient a therapeutically effective amount of a compound according to claim 1.

9. A method of treating a bacterial infection in a patient in need of such treatment, comprising administering to the patient a therapeutically effective amount of a compound according to claim 5.

10. A process for producing a bromotiacumicin compound which comprises culturing a microorganism belonging to the species Dactylosporangium aurantiacum subsp. hamdenensis having the ability to produce a bromotiacumicin compound in a bromide enriched nutrient medium and accumulating a bromotiacumicin compound on said medium.

11. The process as recited in claim 10 wherein said microorganism is Dactylosporangium aurantiacum NRRL 18085.

12. The process as recited in claim 11 wherein said bromotiacumicin is isolated from said culture medium.

13. The process as recited in claim 11 wherein said microorganism is cultured at a temperature of 25° C. to 35° C. and a pH of 6–9 with a bromide salt concentration of from 0.25–1.0%.

14. The process as recited in claim 13 wherein said bromide salt concentration is 0.48%.

* * * * *